US005910411A

United States Patent [19]

Barbosa et al.

[11] Patent Number: 5,910,411
[45] Date of Patent: Jun. 8, 1999

[54] METHOD FOR IDENTIFYING AGENTS THAT MODULATE TRANSCRIPTION OF HUMAN CYTOMEGALOVIRUS POLYMERASE

[75] Inventors: Miguel S. Barbosa; Jun Wu, both of San Diego, Calif.

[73] Assignee: Signal Pharmaceuticals, Inc., San Diego, Calif.

[21] Appl. No.: 08/720,543

[22] Filed: Sep. 30, 1996

[51] Int. Cl.$^6$ .............................. C12Q 1/02; C12Q 1/68; C12N 5/10
[52] U.S. Cl. ................................ 435/6; 435/29; 536/23.5
[58] Field of Search .............................. 435/6, 29, 172.3, 435/320.1, 325, 366, 375; 536/24.1, 23.5, 23.72; 935/33, 34, 36, 70, 71

[56] References Cited

U.S. PATENT DOCUMENTS

| | | | |
|---|---|---|---|
| 4,743,562 | 5/1988 | Rasmussen et al. | 436/518 |
| 5,418,132 | 5/1995 | Olivo | 435/5 |
| 5,591,579 | 1/1997 | Olivo et al. | 435/6 |

FOREIGN PATENT DOCUMENTS 521 427 A1  1/1993  European Pat. Off. .

OTHER PUBLICATIONS

Kerry et al., "Identification of Sequence Elements in the Human Cytomegalovirus DNA Polymerase Gene Promoter Required for Activation by Viral Gene Products," *Journal of Virology* 68(7):4167–4176, 1994.

Kerry et al., "Multiple Regulatory Events Influence Human Cytomegalovirus DNA Polymerase (UL54) Expression during Viral Infection," *Journal of Virology* 70(1):373–382, 1996.

Arlt et al., "Identification of Binding Sites for the 86–Kilodalton IE2 Protein of Human Cytomegalovirus with in an IE2–Responsive Viral Early Promoter," *Journal of Virology* 68(7):4117–4125, 1994.

Klucher et al., "In Vivo and In Vitro Analysis of Transcriptional Activation Mediated by the Human Cytomegalovirus Major Immediate–Early Proteins," *Molecular and Cellular Biology* 13(2):1238–1250, 1993.

Lang et al., "Functional Interaction between the Human Cytomegalovirus 86–Kilodalton IE2 Protein and the Cellular Transcription Factor CREB," *Journal of Virology* 69(10):6030–6037, 1995.

Plachter et al., "Cell Types Involved in Replication and Distribution of Human Cytomegalovirus," *Advances in Virus Research* 46:195–261, 1996.

Baracchini et al., "An Isoform Variant of the Cytomegalovirus Immediate–Early Auto Repressor Functions as a Transcriptional Activator," *Virology* 188:518–529, 1992.

Depto and Stenberg, "Functional Analysis of the True Late Human Cytomegalovirus pp28 Upstream Promoter: cis–Acting Elements and Viral trans–Acting Proteins Necessary for Promoter Activation," *Journal of Virology* 66(5):3241–3246, 1992.

Depto and Stenberg, "Regulated Expression of the Human Cytomegalovirus pp65 Gene: Octamer Sequence in the Promoter Is Required for Activation by Viral Gene Products," *Journal of Virology* 63(3):1232–1238, 1989.

Gribaudo et al., "Interferons Inhibit Onset of Murine Cytomegalovirus Immediate–Early Gene Transcription," *Virology* 197:303–311, 1993.

Hagemeier et al., "The 72K IE1 and 80K IE2 proteins of human cytomegalovirus independently trans–activate the c–fos, c–myc and hsp70 promoters via basal promoter elements," *Journal of General Virology* 73:2385–2393, 1992.

Hagemeirer et al., "The Human Cytomegalovirus 80–Kilodalton but Not the 72–Kilodalton Immediate–Early Protein Transactivates Heterologous Promoters in a TATA Box–Dependent Mechanism and Interacts Directly with TFIID," *Journal of Virology* 66(7):4452–4456, 1992.

Hermiston et al., "Identification and Characterization of the Human Cytomegalovirus Immediate–Early Region 2 Gene That Stimulates Gene Expression from an Inducible Promoter," *Journal of Virology* 61(10):3214–3221, 1987.

Iskenderian et al., "Four of Eleven Loci Required for Transient Complementation of Human Cytomegalovirus DNA Replication Cooperate To Activate Expression of Replication Genes," *Journal of Virology* 70(1):383–392, 1996.

Jenkins et al., "Human cytomegalovirus late protein encoded by ie2: a trans–activator as well as a repressor of gene expression," *Journal of General Virology* 75:2337–2348, 1994.

Kohler et al., "Use of Recombinant Virus To Assess Human Cytomegalovirus Early and Late Promoters in the Context of the Viral Genome," *Journal of Virology* 68(10):6589–6597, 1994.

Leach and Mocarski, "Regulation of Cytomegalovirus Late–Gene Expression: Differential Use of Three Start Sites in the Transcriptional Activation of ICP36 Gene Expression," *Journal of Virology* 63(4):1783–1791, 1989.

Lukac et al., "Transcriptional Activation by the Human Cytomegalovirus Immediate–Early Proteins: Requirements for Simple Promoter Structures and Interactions with Multiple Components of the Transcriptional Complex," *Journal of Virology* 68(8):5184–5193, 1994.

Plachter et al., "Analysis of Proteins Encoded by IE Regions 1 and 2 of Human Cytomegalovirus Using Monoclonal Antibodies Generated against recombinant Antigens," *Virology* 193:642–652, 1993.

(List continued on next page.)

*Primary Examiner*—George C. Elliott
*Assistant Examiner*—Thomas G. Larson
*Attorney, Agent, or Firm*—Seed and Berry LLP

[57] ABSTRACT

Compositions and methods are provided for identifying proteins and other agents that modulate transactivation of HCMV early genes. In particular, agents that inhibit the cell-type specific transactivation of HCMV DNA polymerase are provided. Such agents may be used, for example, in the treatment of patients infected with HCMV.

8 Claims, 7 Drawing Sheets

OTHER PUBLICATIONS

Rüger et al., "Primary Structure and Transcription of the Genes Coding for the Two Virion Phosphoproteins pp65 and pp71 of Human Cytomegalovirus," *Journal of Virology* *61*(2):446–453, 1987.

Scully et al., "The Human Cytomegalovirus IE2 86–Kilodalton Protein Interacts with an Early Gene Promoter via Site–Specific DNA Binding and Protein Associations," *Journal of Virology* *69*(10):6533–6540, 1995.

Stasiak and Mocarski, "Transactivation of the Cytomegalovirus ICP36 Gene Promoter Requires the α Gene Product TRS1 in Addition to IE1 and IE2," *Journal of Virology* *66*(2):1050–1058, 1992.

Stenberg et al., "Promoter–Specific trans Activation and Repression by Human Cytomegalovirus Immediate–Early Proteins Involves Common and Unique Protein Domains," *Journal of Virology* *64*(4):1556–1565, 1990.

Stenberg et al., "Regulated Expression of Early and Late RNAs and Proteins from the Human Cytomegalovirus Immediate–Early Gene Region," *Journal of Virology* *63*(6):2699–2708, 1989.

Stenberg, "The Human Cytomegalovirus Major Immediate–Early Gene," *Intervirology* *39*343–349, 1996.

Stinski and Roehr, "Activation of the Major Immediate Gene of Human Cytomegalovirus by cis–Acting Elements in the Promoter–Regulatory Sequence and by Virus–Specific trans–Acting Components," *Journal of Virology* *55*(2):431–441, 1985.

Thrower et al., "Regulation of a Human Cytomegalovirus Immediate–Early Gene (US3) by a Silencer–Enhancer Combination," *Journal of Virology* *70*(1):91–100, 1996.

METHOD FOR IDENTIFYING AGENTS THAT MODULATE TRANSCRIPTION OF HUMAN CYTOMEGALOVIRUS POLYMERASE

TECHNICAL FIELD

The present invention relates generally to human cytomegalovirus infection. The invention is more particularly related to the identification of proteins and other agents that modulate gene expression necessary for HCMV replication and to the use of such agents in antiviral therapies.

BACKGROUND OF THE INVENTION

Human cytomegalovirus (HCMV) is a ubiquitous member of the herpesvirus family that can induce a wide range of diseases, typically in newborns and immunocompromised adults. Nearly one percent of all live births in the United States are associated with congenital HCMV infection, with approximately 5 to 10 percent of infections resulting in significant neurological defects. In bone marrow transplant recipients, mortality due to HCMV pneumonia can be as high as forty percent. In addition, disseminated HCMV infection is common in AIDS patients and is frequently associated with conditions such as gastroenteritis and sight-threatening chorioretinitis.

The viral genome consists of a large double-stranded DNA molecule of approximately 230 kilobase pairs packaged within an enveloped capsid to form the infectious virion. Productive infection is species- and cell-specific and requires the tightly coordinated sequential expression of viral genes. Viral genes are divided into three kinetic classes: immediate early (IE), early (E) and late (L). The IE gene products, regulated by a complex enhancer promoter, are synthesized immediately after entry of the viral genome into the nucleus of infected cells and rely primarily on host factors for their expression. Transcriptional regulation of IE genes has been extensively studied and three major IE proteins have been characterized: IE72 (IE1 gene region), IE86 (IE2 gene region) and IE55 (IE2 gene region). Early genes are transcribed prior to viral DNA replication. The late genes, which constitute the majority of the viral genome, are transcribed in abundance only after viral DNA replication. Both early and late gene expression is modulated by one or more viral IE proteins, as well as host proteins.

Studies of the biological and biochemical function of IE72, IE86 and IE55 have indicated that these proteins play a critical role in HCMV cascade gene expression. All of these proteins have been shown to be involved in the transactivation of HCMV early promoters, as well as heterologous viral and cellular promoters. IE86 also plays a major role in repressing its own promoter, the major immediate early promoter (MIEP). The IE72 and IE55 proteins act to enhance the activity of the MIEP and augment the stimulatory effect of the IE86 protein on its responsive promoters.

Recently, the IE86 protein was shown to enhance UL112 early promoter activity by binding to discrete sequences. Three IE86 binding sites were identified in this promoter. However, direct binding of IE86 to the promoter is not absolutely required because deletion of these target sites retained 40% of the response to IE86 transactivation (Arlt et al., *J. Virol.* 68:4117–4125, 1994). This transactivation by IE86 appears to involve the interaction of IE86 with the cellular transcriptional factor CREB (Lang et al., *J. Virol.* 69:6030–6037, 1995), which differs from the mechanism of transactivation of the HCMV early promoter UL54 (DNA polymerase, pol). An expression construct encoding the major IE proteins IE72, IE86 and IE55 has been shown to induce transactivation of the pol promoter (see Stenberg et al., *J. Virol.* 64:1556–1665, 1990). However, no IE86 binding sequences have been identified in the promoter. In addition, while HCMV-infected human foreskin fibroblasts showed a DNA binding activity specific for a pol promoter element termed IR1 (see Kerry et al., *J. Virol.* 68:4167–4176, 1994), it is unclear which IE protein plays the central role in DNA binding activity and in promoter activation.

While these and other studies have provided basic information about IE protein function, a greater understanding of the temporal cascade of viral gene expression is required in order to identify suitable targets for drug development. In particular, the identification of cell permissivity factors that are required for productive infection of host cells would provide a basis for the development of new therapeutic drugs. Such drugs are urgently needed for treatment of HCMV strains that are resistant to current therapies, which employ viral polymerase nucleoside analog inhibitors.

Accordingly, there is a need in the art for new therapies for HCMV infection targeting viral molecules necessary for the progression of the viral life cycle. The present invention fulfills these needs and further provides other related advantages.

SUMMARY OF THE INVENTION

Briefly stated, the present invention provides antiviral agents that modulate HCMV pol transactivation. In one aspect, the present invention provides methods for identifying an agent that modulates transcription of HCMV DNA polymerase, comprising: (a) transfecting a permissive or nonpermissive cell expressing IE86 and a reporter gene, wherein the reporter gene is under the control of the HCMV DNA polymerase promoter, with a polynucleotide encoding a candidate agent; and (b) evaluating the effect of said candidate agent on reporter gene transcription, and therefrom identifying an agent that modulates transcription of HCMV DNA polymerase.

In related aspects, methods for identifying an agent that modulates transcription of HCMV DNA polymerase are provided, comprising: (a) contacting a permissive or nonpermissive cell expressing IE86 and a reporter gene, wherein the reporter gene is under the control of the HCMV DNA polymerase promoter, with a candidate agent; and (b) evaluating the effect of said candidate agent on reporter gene transcription, and therefrom identifying an agent that modulates transcription of HCMV DNA polymerase.

In further aspects, modulating agents that inhibit transactivation of HCMV DNA polymerase by IE86 in permissive cells are provided.

In other aspects, methods for treating HCMV infection in a patient are provided. Such methods may comprise administering to a patient an agent that inhibits transactivation of HCMV DNA polymerase by IE86 in permissive cells. Alternatively, such methods may comprise administering to a patient a polynucleotide encoding an agent that inhibits transactivation of HCMV DNA polymerase by IE86 in permissive cells.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS 1A–1D illustrate the activation of the HCMV pol promoter by IE86.

FIGS. 3A–3D are graphs and autoradiograms depicting the level of early promoter activation in representative permissive and nonpermissive cells stably expressing IE86.

FIGS. 4A and 4B are autoradiograms presenting the results of electrophoretic mobility-shift assays using the IR1 element and nuclear extracts from IE86-expressing and parental U373 MG and HeLa cells.

In FIG. 5A, lane 1 shows the control (no extract added), lane 2 shows the binding in the absence of IE86 and lane 3 shows the binding in cells expressing IE86. The location of the specific complex is indicated with the arrow and nonspecific complexes are also shown. FIG. 5B shows the binding in the presence of IE86 without competitor (lane 1), with wildtype IR1 element competitor (lane 2) and with mutant IR1 element competitor (lane 3). FIG. 5C shows the binding in the presence of IE86 without antibody (lane 4), with MAB810 antibody (lane 5), with p65Ab (lane 6) or with p50Ab (lane 7).

DETAILED DESCRIPTION OF THE INVENTION

As noted above, the present invention is generally directed to proteins and other agents for use in the treatment of HCMV infection. In particular, the present invention is directed to methods for identifying and purifying agents that modulate IE86 transactivation of HCMV DNA polymerase (UL54, pol) in permissive and nonpermissive cells. The present invention is also directed to compositions comprising such agents, which may be used in the treatment of patients infected with HCMV.

It has been found, within the context of the present invention, that IE86 is the major IE protein responsible for transactivation of pol (see FIGS. 1A–1D). Transfection of permissive cells containing the pol promoter with a construct containing IE86 cDNA under the control of a heterologous promoter (e.g., Rous Sarcoma Virus promoter) is generally sufficient for pol promoter transactivation. In contrast, similar constructs containing IE72 or IE55 cDNA do not transactivate pol, and cotransfection of IE86 with IE72 and/or IE55 expression constructs shows no significant activation over the levels observed in the presence of IE86 alone. Expression constructs containing IE86, IE72 and/or IE55 cDNA may generally be prepared and used to transfect cells (Baracchini et al., Virol. 188:518–529, 1992; Depto and Stenberg, J. Virol. 63:1232–1238, 1989). The level of pol transactivation may generally be determined using, for example, a PCR-amplified pol promoter region controlling expression of a reporter gene (e.g., luciferase). A HCMV pol promoter region may be amplified from HCMV nucleic acid obtained from any of a variety of sources (such as Advanced Biotechnologies, Inc., Columbia, Md.) using primers derived from the sequence (−425 to +15; see Stenberg, "Sequence-specific activation of CMV early promoters. Molecular aspects of human cytomegalovirus diseases" E. -S. Huang. New York, Springer-Verlag 2:349–351, 1992) and methods well known to those of ordinary skill in the art. A reporter gene may be placed under the control of the pol promoter using, for example, any of a variety of commercially available vectors (such as the pGL-2 basic luciferase reporter plasmid, available from Promega, Madison, Wis.) using standard techniques.

Surprisingly, it has also been found within the context of the present invention, that activation of the pol promoter by IE86 is cell type-specific. In other words, while IE86 transactivates the early promoter UL112 in both permissive cells (e.g., U373 MG glial cells, macrophages, human foreskin or embryonic primary or immortalized fibroblasts, bone marrow stem cells, endometrial stromal cells and/or brain endothelial cells) and non-permissive cells (e.g., HeLa and C33-A epithelial cells), IE86 transactivates pol only in permissive cells (see FIGS. 2A–2C and 3A–3D). This transactivation appears to be mediated by the IR1 element, which is specifically bound by a complex containing IE86 in permissive cells (see FIGS. 4A–4B and 5A–5C). The IR1 element has been described by Kerry et al., J. Virol. 68:4167–4176, 1994.

As noted above, the present invention is directed to the development of modulating agents. Within the context of the present invention, a "modulating agent" is any compound that is capable of enhancing or, preferably, inhibiting the cell-specific transactivation of pol by IE86. A modulating agent may act directly by interacting with IE86 and/or the pol promoter or by inhibiting expression of IE86. Alternatively, a modulating agent may act indirectly by inhibiting or enhancing the activity of one or more other proteins which, in turn, modulate IE86 transactivation. For inhibition, a modulating agent typically has an $IC_{50}$ of less than 1 μM, and preferably 1–200 nM. Modulating agents may include antibodies (e.g., monoclonal), polynucleotides, endogenous cellular factors and other drugs. Polynucleotides encoding such modulating agents are also encompassed by the present invention.

In general, modulating agents may be identified using any of a variety of techniques known to those of ordinary skill in the art. For example, to identify an agent that inhibits pol transactivation, a permissive cell containing an expression vector that produces IE86 may be transfected with a reporter gene under the control of the HCMV pol promoter, such that the pol promoter is activated in the absence of modulating agent. Such a cell may then be exposed to a candidate modulating agent under conditions and for a time sufficient to allow the candidate agent to inhibit activation of the pol promoter. Similarly transfected nonpermissive cells may be used to identify agents that enhance pol transactivation or for further study of the function of a candidate agent. A stable cell line that expresses IE86 may be established using techniques well known to those of ordinary skill in the art. For example, cells may be cotransfected with an expression vector that produces IE86 and a selection plasmid, and transfected cells selected and expanded. Any of a variety of reporter genes known to those of ordinary skill in the art (e.g., the luciferase gene) may be linked to the pol promoter and transfected into such IE86-expressing cells using standard techniques.

Transfected cells may then be exposed to a candidate modulating agent for a suitable amount of time, and the effect of the candidate agent on transactivation may be evaluated by measuring the level and/or activity of the reporter protein. Standard techniques may be employed, such as PCR or hybridization (for evaluating levels of mRNA) or any of a variety of immunoassays or functional assays appropriate for the reporter protein employed. For example, expression of the luciferase (luc) reporter gene may be measured using commercially available assays (obtainable from, e.g., Analytical Luminescence Laboratory, Ann Arbor, Mich.). Alternatively, endogenous modulating agents may be identified by, for example, using a two-hybrid screen to identify proteins that interact with IE86 or by standard mutagenesis and complementation methods. Such modulating agents may then be purified from cellular extracts based on affinity for IE86 or using other biochemical techniques, using methods well known to those of ordinary skill in the art. It will be readily apparent to those of ordinary skill in the art that derivatives of IE86 may also be employed in such purification procedures. For example, portions of IE86 may be suitable. Specific regions responsible for interaction with cellular factors may be identified using standard deletion mapping techniques, which are well known to those of ordinary skill in the art. In addition, or alternatively, sequences may be added to the N- or C-terminus to aid in the preparation and/or use of the derivative for affinity procedures.

Antibody modulating agents encompassed by the present invention may be polyclonal or monoclonal, and may be specific for IE86 or for another protein involved in IE86 transactivation. Preferred antibodies are those antibodies that inhibit IE86 transactivation. Antibodies may be prepared by any of a variety of techniques known to those of ordinary skill in the art (see, e.g., Harlow and Lane, Antibodies: A Laboratory Manual, Cold Spring Harbor Laboratory, 1988). In one such technique, an immunogen comprising IE86 or a portion thereof is initially injected into a suitable animal (e.g., a mouse, rat, rabbit, sheep or goat), preferably according to a predetermined schedule incorporating one or more booster immunizations, and the animal is bled periodically. Polyclonal antibodies specific for IE86 may then be purified from such antisera by, for example, affinity chromatography using IE86 coupled to a suitable solid support.

Monoclonal antibodies specific for IE86 may be prepared, for example, using the technique of Kohler and Milstein, Eur. J. Immunol. 6:511–519, 1976, and improvements thereto. Briefly, these methods involve the preparation of immortal cell lines capable of producing antibodies having the desired specificity (ie., reactivity with IE86). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Antibodies may then be tested for their ability to function as modulating agents, as described above.

Modulating agents may also be endogenous cellular factors or other proteins. For example, an agent that inhibits pol transactivation may be a protein present in nonpermissive cells. Such modulating agents may generally be identified by transfecting a permissive cell expressing IE86 and a reporter gene under the control of the HCMV DNA polymerase promoter with a polynucleotide encoding a protein present in nonpermissive cells (e.g., cDNA prepared from nonpermissive cells). The effect of the encoded protein on reporter gene transcription may then be evaluated as described above.

In another aspect of the present invention, one or more modulating agents as described above may be used to treat a patient infected with HCMV. For administration to a patient, one or more modulating agents are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a modulating agent, such that the modulating agent is generated in situ, in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–1749 (1993).

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey munne sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for modulating agents is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well as doses, will vary from patient to patient. In general, the pharmaceutical compositions may be administered intravenously, intraperitoneally, intramuscularly, subcutaneously, intracavity or transdermally. Typically, between two and three doses may be administered every day for a period of about two weeks. A suitable dose is an amount of a modulating agent or polynucleotide encoding a modulating agent that is sufficient to induce a decrease in the level of infection and/or improvement in the symptoms of a patient afflicted with HCMV infection. Such improvement may be detected by monitoring of viral levels using standard techniques, such as cell based viral assays, PCR and viral culture methods, or through an improvement in clinical symptoms associated with the disease. In general, the amount of polypeptide present in a dose, or produced in situ by DNA present in a dose, ranges from about 0.5 mg to about 250 mg per kg of host, preferably from about 5 mg/kg to about 50 mg/kg. Suitable dose sizes will vary with the size of the patient, but will typically range from about 0.5 mL to about 5 mL for 10–60 kg animal.

The following Examples are offered by way of illustration and not by way of limitation.

EXAMPLES

Example 1

Identification of IE86 as a Major Transactivator of HCMV DNA Polymerase

To identify the transactivating IE protein, it was first determined that the pol promoter construct responded to immediate early proteins as previously reported. The UL54 (Pol) promoter sequence, from position −425 to +15, was amplified by PCR using cosmid pCM1058 (a gift from Peter Ghazal, The Scripps Research Institute, La Jolla, Calif.) as a template. The oligonucleotide primer sequences used were:

5'-CCCAAGCTTGGGGGAATTCAACTCGTACAAG-CAG-3' (sense) (SEQ ID NO: 1), and

5'-CCCAAGCTTGGGTCAGACGACGGTGGTCCC-3' (antisense) (SEQ ID NO: 2).

These oligonucleotide primers introduced a HindIII restriction site at the 5' and 3' ends of the UL54 (Pol) promoter fragment allowing insertion into the pGL2-basic luciferase reporter plasmid (Promega, Madison, Wis.). The PCR fidelity of UL54 (Pol) promoter sequence was confirmed by sequencing. Expression vectors for each of the HCMV immediate early proteins, RSV IE72, RSV IE86, RSV IE55 (gifts from Peter Ghazal; see Baracchini et al., Virol. 188:518–529, 1992), and pSVH, which expresses proteins from the major IE gene region have been described (Depto et al., J. Virol. 63:1232–1238, 1989).

U373 MG cells were cotransfected with the reporter construct, and with increasing amounts of pSVH and a LacZ gene expression vector (Promega. Madison, Wis.), using the Profection™ mammalian transfection system (Promega, Madison, Wis. Cat# E1200). Fourteen to sixteen hours posttransfection, cells were harvested and assayed for luciferase activity as prescribed by the manufacturer (Analytical Luminescence Laboratory, Ann Arbor, Mich.) and for β-gal activity as prescribed by the manufacturer (Promega, Madison, Wis.). Luciferase activity, normalized to the β-gal activity, is presented in FIG. 1A. These results show that cotransfection with pSVH, a construct encoding the three immediate early genes (IE72, IE86 and IE55) from the endogenous genomic fragment under control of its own major immediate early promoter, resulted in strong activation of the pol promoter as measured by expression of the luciferase reporter. Thus, the pol-luciferase reporter construct carries all regulatory elements previously shown to mediate the response to the immediate early proteins expressed from the pSVH expression vector.

Figure 1A:
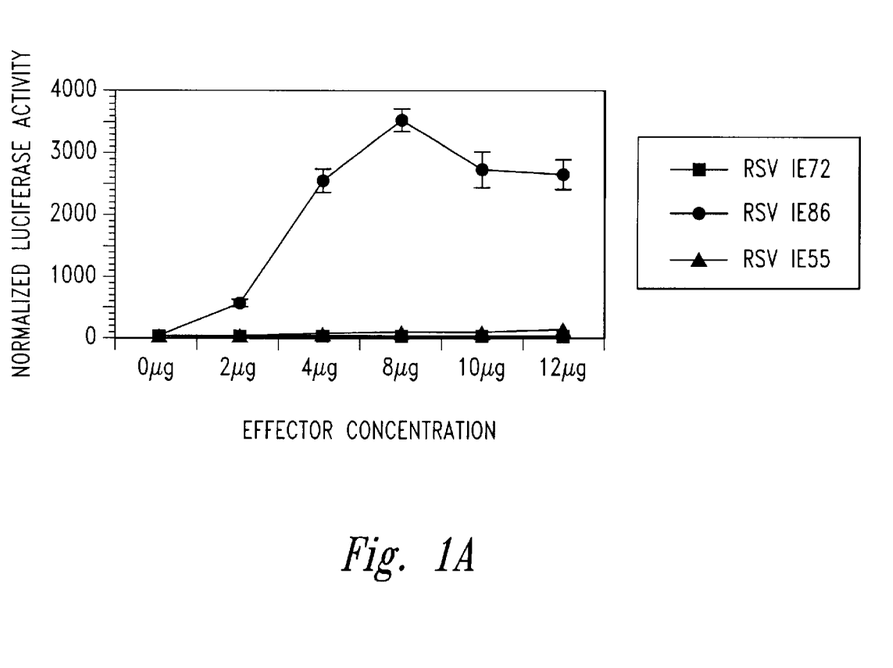
FIG. 1A is a graph depicting the level of luciferase activity in U373 MG cells cotransfected with Pol-luciferase reporter and increasing amounts of IE72, IE86 or IE55 expression vectors (as indicated), along with a LacZ gene expression vector. Luciferase activity was normalized to the beta-galactosidase activity.
Figure 1B:
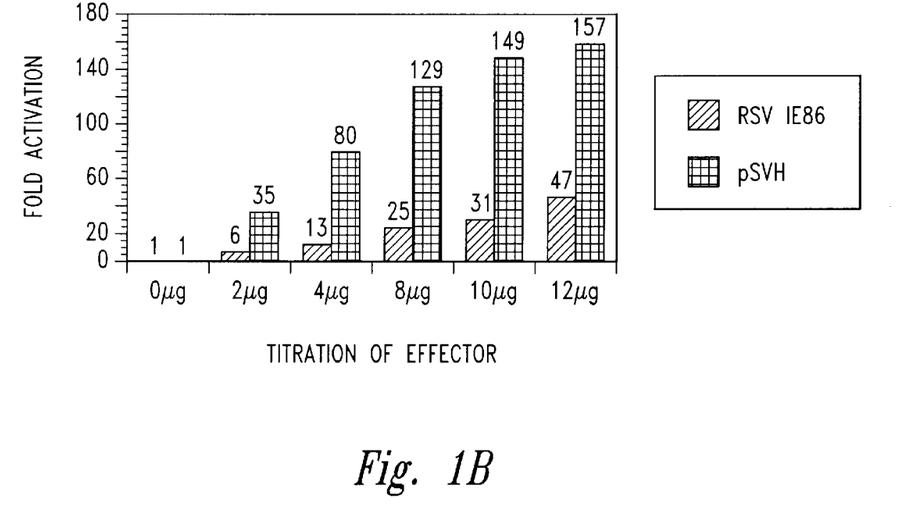
FIG. 1B is a histogram showing the fold activation of pol-luciferase by increasing amounts of IE86 or pSVH (which expresses proteins from the major IE gene region).

Separate transfections were then performed using each of three expression constructs encoding the IE72, IE55 and IE86 cDNA sequences under control of the heterologous Rous Sarcoma Virus promoter. Transfections were performed as described above. Interestingly, only the IE86 expression vector was capable of activating the pol promoter (FIG. 1B). Neither the IE72 nor the IE55 expression vectors yielded significant activation of the pol promoter (FIG. 1B).

Comparison of pol promoter activation by cotransfection with pSVH and RSVIE86 showed about three-fold stronger effect by the former expression vector. Therefore, assays were performed for the level of immediate early protein expression by the different expression vectors using Western analyses. For each sample, 25 μg of total protein were separated by SDS-polyacrylamide electrophoresis and transferred to Hybond™-ECL nitrocellulose membrane (Amersham, Arlington Heights, Ill.). Monoclonal antibody MAB 810 against HCMV immediate early proteins (Chemicon, Temecula, Calif.), was used. Proteins bound by primary antibodies were detected with a secondary antibody conjugated with alkaline phosphatase according to the manufacturer's protocol (Amersham, Arlington Heights, Ill.).

Figure 1C:
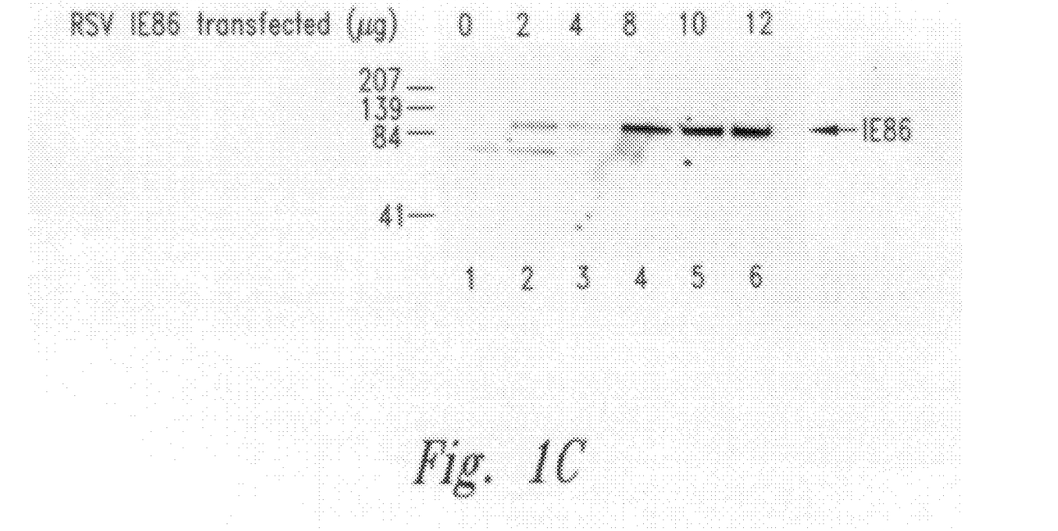
FIG. 1C is an autoradiogram showing the level of IE86 in U373 cells transfected with increasing amounts of IE86 expression vector, as indicated.
Figure 1D:
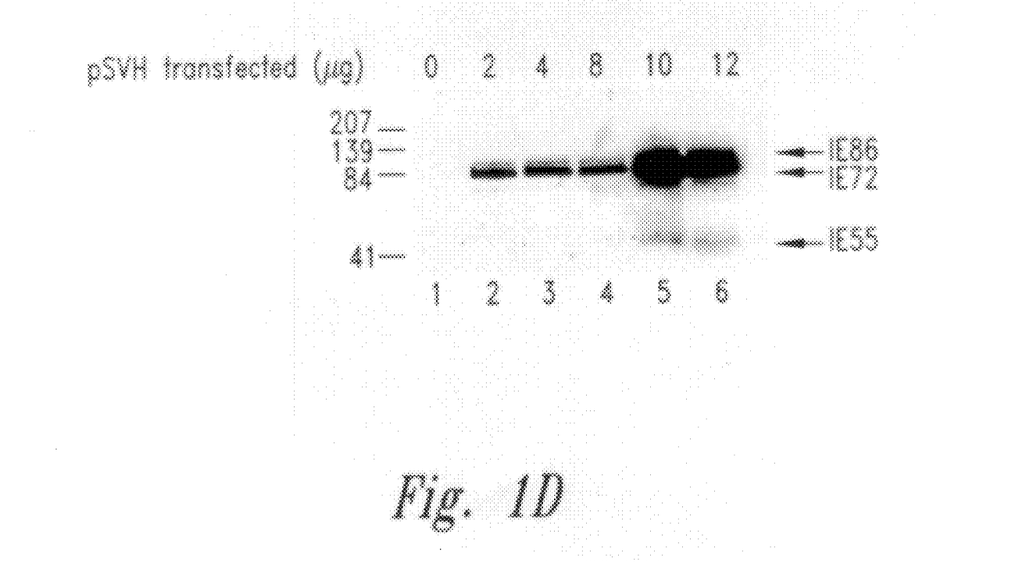
FIG. 1D is an autoradiogram showing the level of IE86, IE72 and IE55 in U373 cells transfected with increasing amounts of pSVH expression vector, as indicated. Arrows indicate the location of the different IE proteins.

These analyses indicate that IE86 protein levels are higher in cells transfected with the pSVH vector than in cells transfected with RSVIE86 (FIG. 1C). In addition, cotransfection of RSVIE86 with RSVIE72 and/or RSVIE55 showed no significant activation over the levels seen in presence of IE86 alone (data not shown). Therefore, the IE86 immediate early protein is the major factor responsible for transactivation of the pol promoter.

Example 2

Cell Type-Specific Activation of the Pol Promoter by IE86

This Example illustrates the ability of IE86 to transactivate the pol promoter in a cell-specific manner.

The response of two early gene promoters, pol and UL112, to IE86 expression in permissive and nonpermissive cells was analyzed. UL112 promoter sequence from −352 to +37 was amplified by PCR using cosmid pCM1058 as a template. The primer sequences for the UL112 promoter were:

5'-CGGGGTACCCCGCACAGAGGTAACAAC-3' (sense) (SEQ ID NO: 3); and

5'-GAAGATCTTCGGCGGTGGAGCGAGTGC-3' (antisense) (SEQ ID NO: 4).

These primers introduced KpnI and BglII restriction sites at the 5' and 3' ends of the UL112 promoter fragment, respectively, allowing directional insertion into the pGL2-basic luciferase reporter plasmid (Promega, Madison, Wis.). Transfection of U373 MG, HeLa and C33-A cells with reporter constructs and increasing amounts of the IE86 construct (RSVIE86) and LacZ expression vector were performed as described above. Luciferase activities normalized to the β-galactosidase activity are shown in FIGS. 2A–2C.

Figure 2A:
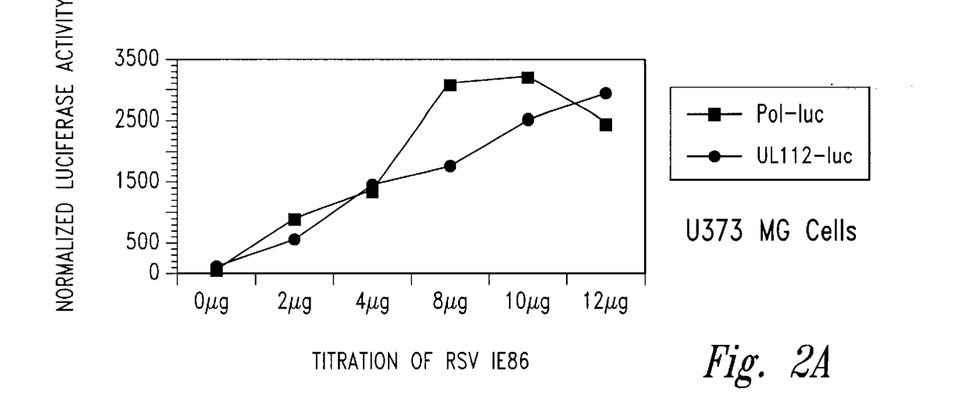
FIGS. 2A–2C are graphs depicting the level of luciferase activity in U373 MG cells (FIG. 2A), HeLa cells (FIG. 2B) and C33-A cells (FIG. 2C) cotransfected with pol-luciferase or UL112-luciferase and increasing amounts of RSV IE86, as indicated, and a LacZ gene expression vector. Luciferase activity was normalized to the beta-galactosidase activity.
Figure 2B:
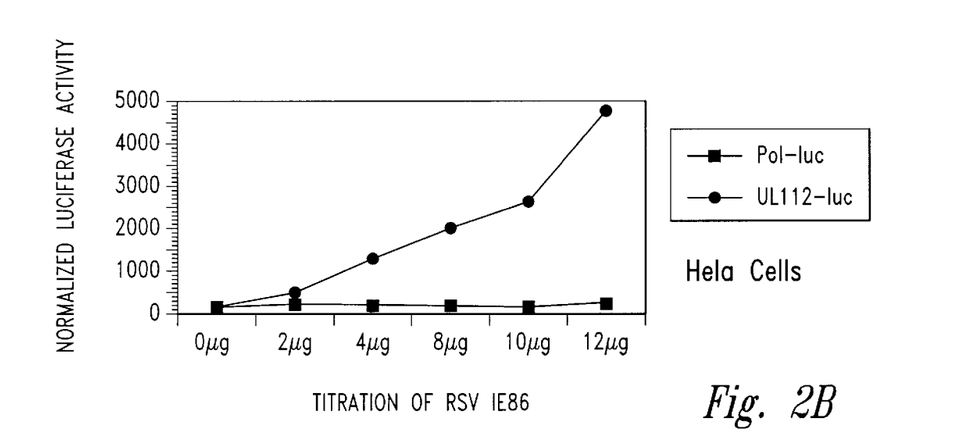
Figure 2C:
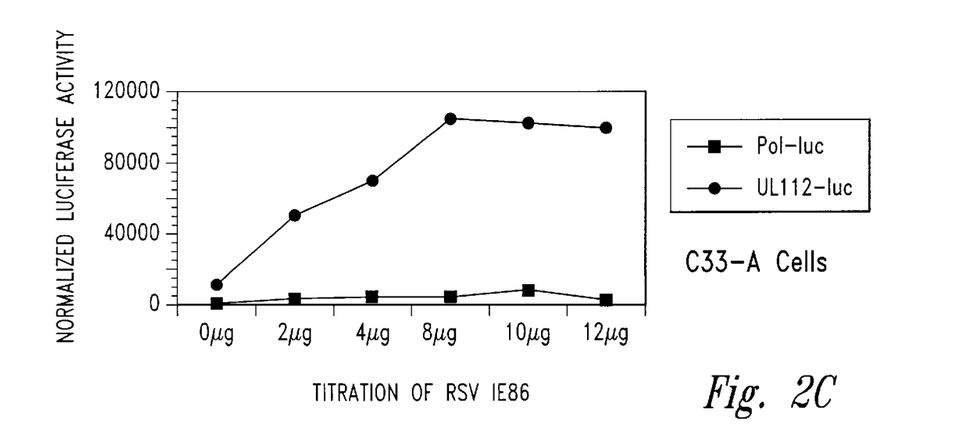

In the permissive U373 MG glial cells, both promoters were efficiently activated by cotransfected RSVIE86 (FIG. 2A). However, no activation of the pol promoter was detected in the nonpermissive HeLa or C33-A epithelial cells (FIGS. 2B and 2C). In contrast, the UL112 reporter was transactivated in nonpermissive cells by cotransfection with RSVIE86 (FIGS. 2B and 2C). The lack of luciferase expression from the pol-luciferase reporter is not simply due to inefficient transfection, since the data shown are normalized for the β-galactosidase levels expressed by a cotransfected control plasmid and the UL112-luciferase reporter was still activated by IE86 in those cells.

To confirm the cell-specific activation, the same reporter plasmids were tested in cell lines stably expressing the IE86 protein. To establish U373 MG and HeLa stable cell lines expressing IE86, the RSV IE86 and pSV2Neo (Clontech Laboratories, Inc., Palo Alto, Calif.) selection plasmids were cotransfected into U373 MG and HeLa cells by the calcium phosphate method. Transfectants were selected in medium containing 0.6 mg/ml G418 on the third day after transfection. G418-resistant clones were expanded and 3×10$^4$ cells seeded in triplicate in a 96 well plate. Cells were harvested and assayed for IE86 by Western blot analysis as described above. Clones showing expression of IE86 protein were amplified and used for further studies.

Figure 3A:
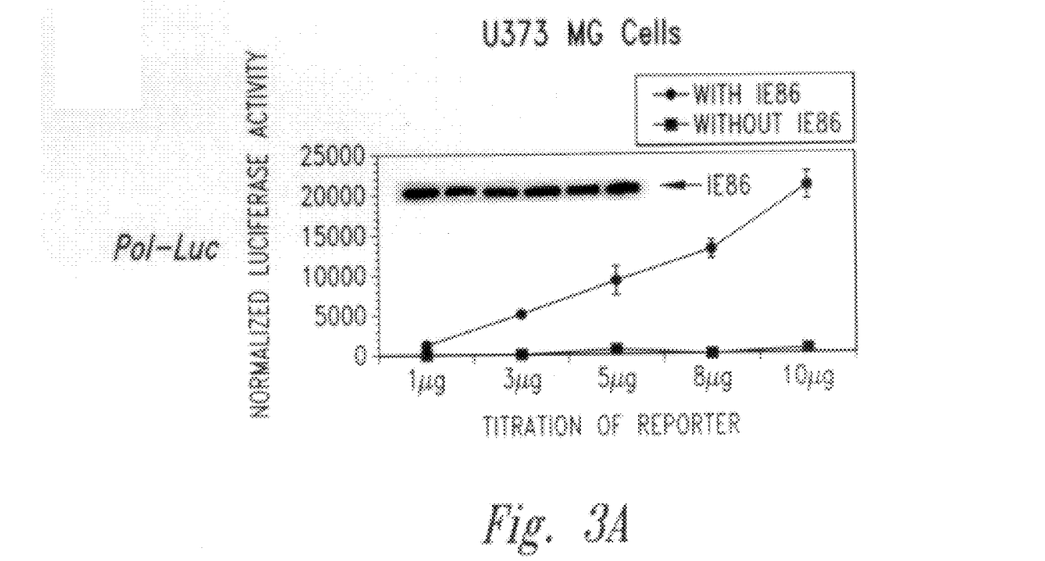
FIG. 3A is a graph showing the level of luciferase activity in U373 MG cells transfected with increasing amounts of pol-luciferase, along with an autoradiogram depicting the level of IE86 expressed by the stable cell line, as determined by Western blot analysis.
Figure 3B:
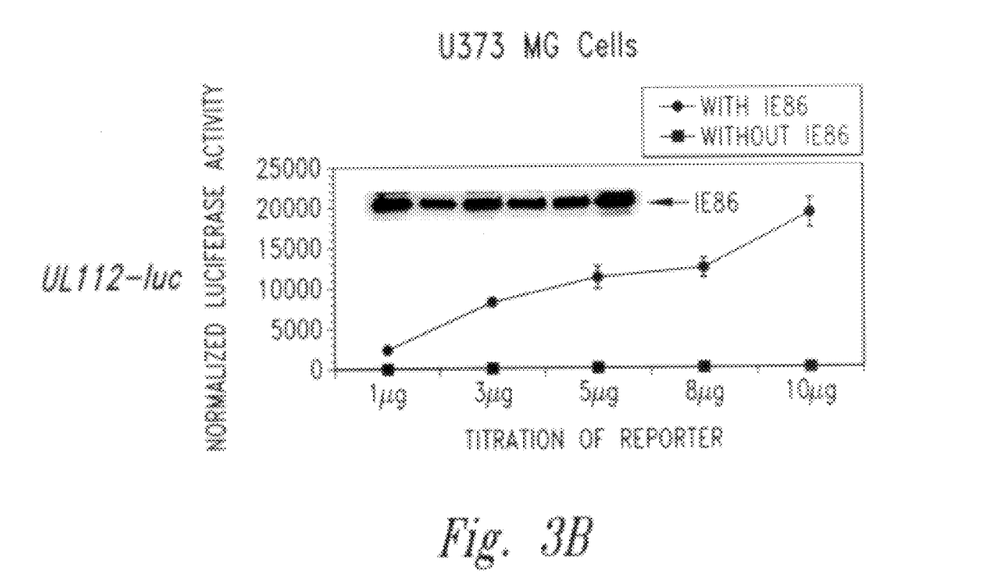
FIG. 3B shows the level of luciferase activity in U373 MG cells transfected with increasing amounts of UL112-luciferase, along with the level of IE86.
Figure 3C:
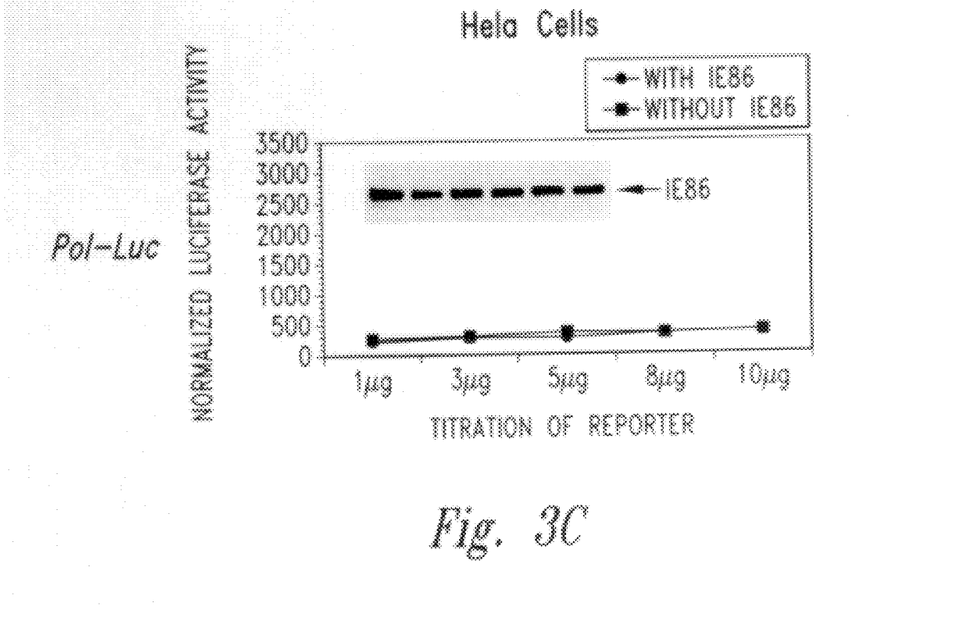
FIG. 3C shows the level of luciferase activity in HeLa cells transfected with increasing amounts of pol-luciferase, along with the level of IE86.
Figure 3D:
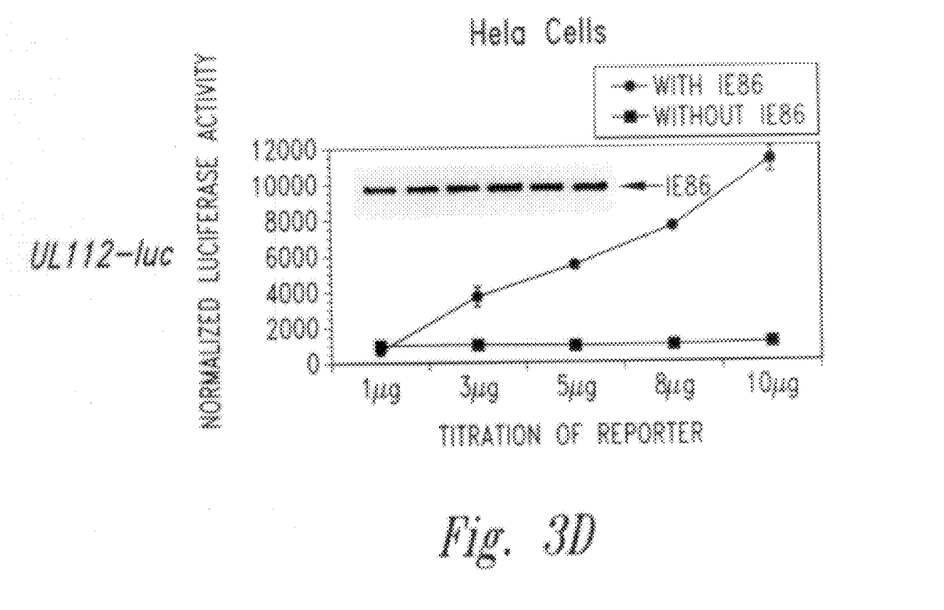
FIG. 3D shows the level of luciferase activity in HeLa cells transfected with increasing amounts of UL112-luciferase, along with the level of IE86.

U373 MG and HeLa cell clones constituitively expressing similar amounts of IE86 were then transfected with increasing amounts of the pol-luciferase and UL112-luciferase reporters. Cells were then harvested for the luciferase activities as described above. Although the levels of IE86 protein expressed were identical (as determined by Western blot using MAB 810 against the IE proteins as described above), the luciferase reporter protein encoded in the pol promoter plasmid was only expressed in U373 MG and not in HeLa cells (FIGS. 3A and 3C). Transfection with the UL112-luciferase reporter plasmid showed significant activation in both U373 MG and HeLa cells expressing IE86 protein (FIGS. 3B and 3D). Therefore, IE86 transactivates the pol promoter in a cell specific manner.

Example 3

Identification of a Cell Specific Binding Activity to the Inverted Repeat (IR1) Element This Example illustrates the cell specific binding of a complex containing IE86 to the inverted repeat element (IR1) of the pol promoter reported by Kerry et al., J. Virol. 68:4167–4176, 1994.

Electrophoretic mobility-shift assays were conducted with radioactively labeled IR1 oligonucleotides and nuclear extracts from IE86-expressing and parental U373 MG and HeLa cells. U373 MG, U373 IE86, HeLa, and HeLa IE86 nuclear extracts were prepared by the Dignam procedure (Dignam et al., *Nucl. Acids Res.* 11: 1475–1489, 1983). For the gel mobility shift assay, the oligonucleotide containing the IR1 element (Kerry et al., *J. Virol.* 68:4167–4176, 1994) was labeled at the 5' end with [γ-$^{32}$P] ATP. 5 μg of nuclear extracts were incubated with 1 μg of poly(dI:dC) poly (dI:dC) and 10,000 cpm of labeled IR1 oligo for 30 min at room temperature in binding buffer (75 mM NaCl, 15 mM Tris, pH7.5, 1.5 mM EDTA, 1.5 mM DTT, 7.5% glycerol, 0.3% NP-40, 20 μg BSA). 4% polyacrylamide gel was pre-run in standard 0.25× Tris-borate-EDTA at 150 V for at least 1.5 hrs. Sample reactions were then subjected to polyacrylamide gel electrophoresis. Gels were dried and subjected to autoradiography. In competition and antibody super-shift experiments (described below), a 50-fold excess of unlabeled oligo and 1 μg of specific (MAB 810 as described above) and non-specific (p65 and p50 against NFκB, Santa Cruz Biotechnology, Santa Cruz, Calif.) monoclonal antibodies were used.

Figures 4A, 4B:
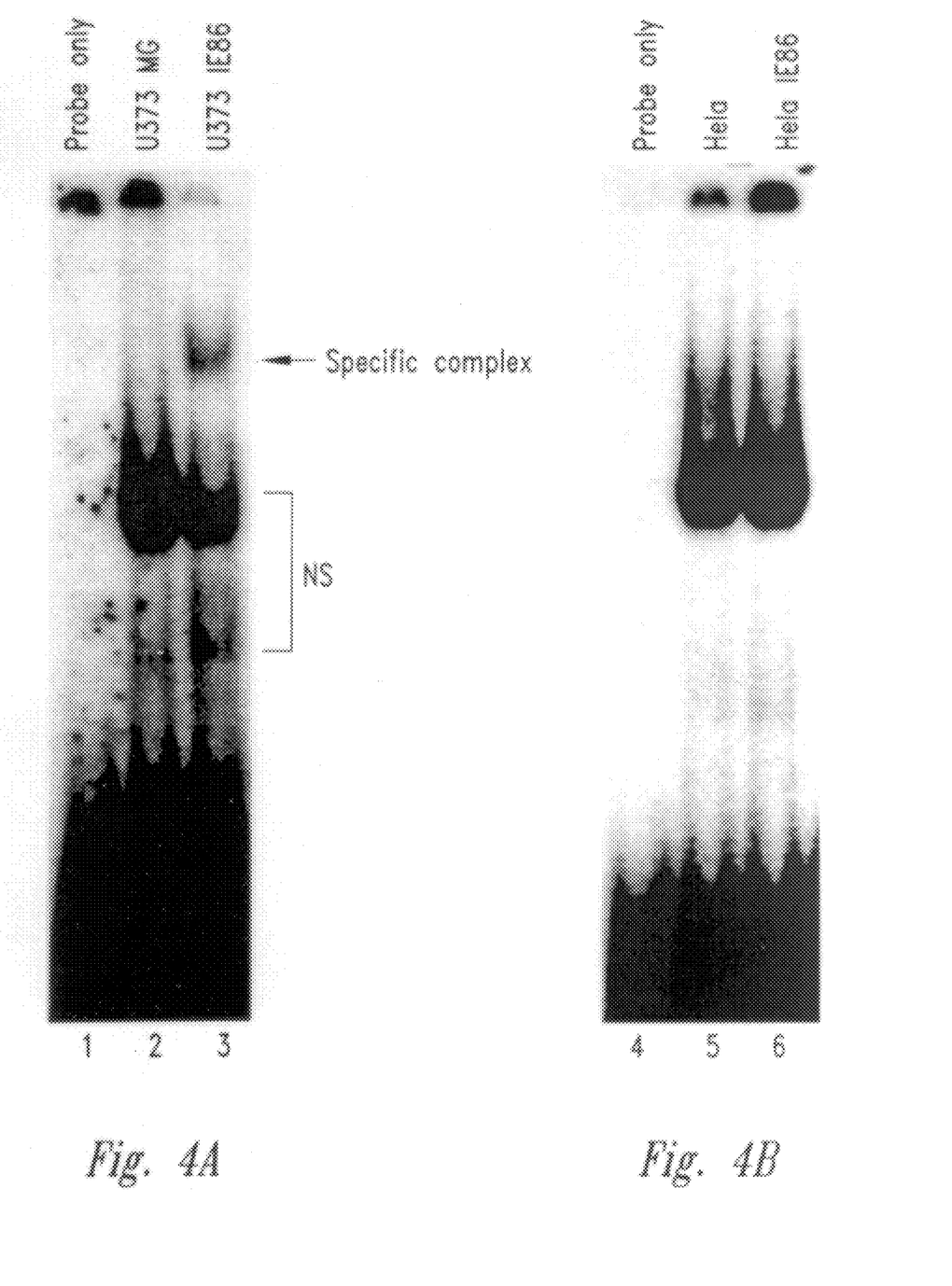
FIG. 4A shows the results for U373 MG cells, where lane 1 shows the control (no extract added), lane 2 shows the binding in the absence of IE86 and lane 3 shows the binding in cells expressing IE86. The location of the specific complex is indicated with the arrow and nonspecific complexes are also shown.
FIG. 4B shows the results for HeLa cells, where lane 1 shows the control (no extract added), lane 2 shows the binding in the absence of IE86 and lane 3 shows the binding in cells expressing IE86.

A specific complex was present in IE86-expressing U373 MG cells but not in extracts from the parental cell (FIG. 4A). In comparison, HeLa cells did not show the complex in the presence or absence of IE86 (FIG. 4B). The absence of the IE86 specific complex in HeLa cells is not due to a lack or lower level of IE86 protein since, as shown in FIG. 3, the protein is expressed at similar levels in U373 MG cells.

Figures 5A, 5B:
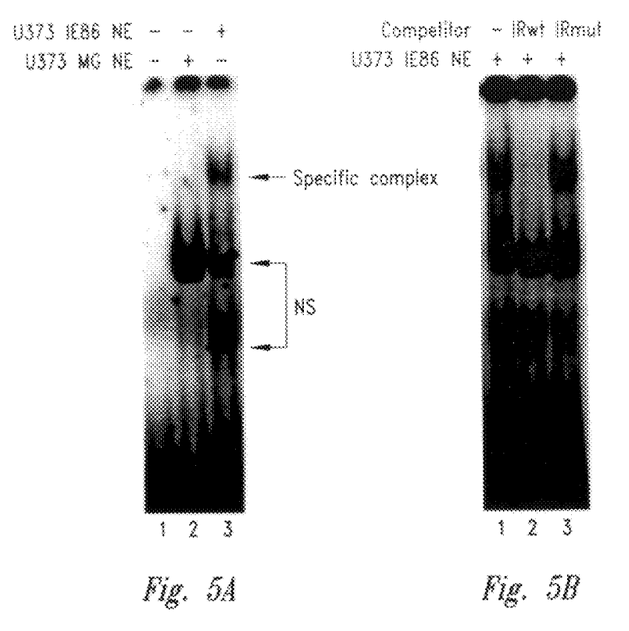
FIGS. 5A–5C are autoradiograms depicting the results of electrophoretic mobility-shift assays using nuclear extracts from IE86-expressing U373 MG cells and the IR1 element (FIG. 5A), the IR1 element and nonlabeled IR1 wildtype or mutant oligonucleotides (FIG. 5B) or the IR1 element with specific or nonspecific monoclonal antibodies (FIG. 5C).

The band seen in IE86 expressing U373 MG cell extracts was then determined to be specific for the IR1 element. While the wild-type IR1 oligonucleotide was able to compete out the formation of the radiolabeled IR1 oligonucleotide with the factors in the IE86-expressing U373 MG cell extracts, a similar amount of oligonucleotide carrying a mutation in the IR1 sequence (Kerry et al., *J. Virol.* 68:4167–4176, 1994) was not (FIG. 5B). Therefore, the DNA complex formed in extracts from U373 MG cells expressing the IE86 protein is specific for the IR1 element.

Figure 5C:
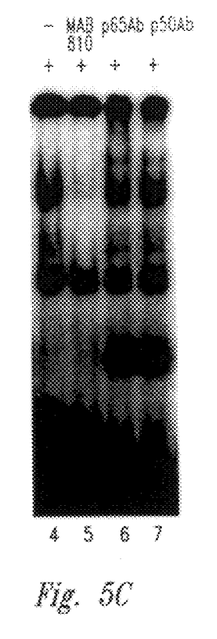

To determine whether the IE86 protein itself is part of the complex, the electrophoretic mobility shift assays were repeated with extracts from the IE86 expressing U373 MG cells in the absence and presence of different monoclonal antibodies. As shown in FIG. 5C, addition of a monoclonal antibody that recognizes IE86 (MAB810) disrupts the IR1 specific complex. In contrast, two other monoclonal antibodies specific for the cellular transcription factor NF-κB (p65Ab and p50Ab) had no effect on the IR1 complex. These results suggest that the viral immediate early protein is present in the specific DNA-binding complex. This conclusion is further supported by western analysis of the shifted band with the IE86 specific monoclonal antibody (data not shown). Thus, the data indicate that IE86 is present in the cell-specific complex associated with the IR1 element.

From the foregoing, it will be appreciated that, although specific embodiments of the invention have been described herein for the purpose of illustration, various modifications may be made without deviating from the spirit and scope of the invention.

We claim:

1. A method for identifying an agent that modulates transcription of HCMV DNA polymerase, comprising:
   (a) transfecting a cell permissive for HCMV replication, wherein the cell expresses IE86 and a reporter gene, and wherein the reporter gene is under the control of an HCMV DNA polymerase promoter, with a polynucleotide encoding a candidate agent for modulating transcription of HCMV DNA polymerase; and
   (b) evaluating the effect of said candidate agent on reporter gene transcription, wherein modulation of reporter gene transcription by said candidate agent is indicative of the ability to modulate HCMV DNA polymerase transcription, and therefrom identifying an agent that modulates transcription of HCMV DNA polymerase.

2. A method according to claim 1 wherein said polynucleotide encodes a protein present in cells that are not permissive for HCMV replication.

3. A method according to claim 2 wherein said agent inhibits transcription of said reporter gene.

4. A method for identifying an agent that modulates transcription of HCMV DNA polymerase, comprising:
   (a) transfecting a cell that is not permissive for HCMV replication, wherein the cell expresses IE86 and a reporter gene, and wherein the reporter gene is under the control of an HCMV DNA polymerase promoter, with a polynucleotide encoding a candidate agent for modulating transcription of HCMV DNA polymerase; and
   (b) evaluating the effect of said candidate agent on reporter gene transcription, wherein modulation of reporter gene transcription by said candidate agent is indicative of the ability to modulate HCMV DNA polymerase transcription, and therefrom identifying an agent that modulates transcription of HCMV DNA polymerase in permissive cells.

5. A method according to claim 4 wherein said candidate agent is a protein present in cells permissive for HCMV replication.

6. A method for screening for an agent that modulates transcription of HCMV DNA polymerase, comprising:
   (a) contacting a cell permissive for HCMV replication, wherein the cell expresses IE86 and a reporter gene, and wherein the reporter gene is under the control of an HCMV DNA polymerase promoter, with a candidate agent for modulating transcription of HCMV DNA polymerase; and
   (b) evaluating the effect of said candidate agent on reporter gene transcription, wherein modulation of reporter gene transcription by said candidate agent is indicative of the ability to modulate HCMV DNA polymerase transcription, and therefrom identifying an agent that modulates transcription of HCMV DNA polymerase.

7. A method according to claim 6 wherein said agent inhibits reporter gene transcription.

8. A method for screening for an agent that modulates transcription of HCMV DNA polymerase, comprising:
   (a) contacting a cell that is not permissive for HCMV replication, wherein the cell expresses IE86 and a reporter gene, and wherein the reporter gene is under the control of an HCMV DNA polymerase promoter, with a candidate agent for modulating transcription of HCMV DNA polymerase; and
   (b) evaluating the effect of said candidate agent on reporter gene transcription, wherein modulation of reporter gene transcription by said candidate agent is indicative of the ability to modulate HCMV DNA polymerase transcription, and therefrom identifying an agent that modulates transcription of HCMV DNA polymerase.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear    (xi) SEQUENCE DESCRIPTION: SEQ ID NO:1:

CCCAAGCTTG GGGGAATTCA ACTCGTACAA GCAG          34

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear    (xi) SEQUENCE DESCRIPTION: SEQ ID NO:2:

CCCAAGCTTC CCTCAGACGA CGGTGGTCCC          30

(2) INFORMATION FOR SEQ ID NO:3:

(i) SEQUENCE CHARACTERISTICS:
      (A) LENGTH: 27 base pairs
      (B) TYPE: nucleic acid
      (C) STRANDEDNESS: single
      (D) TOPOLOGY: linear -continued (xi) SEQUENCE DESCRIPTION: SEQ ID NO:3:

CGGGGTACCC CGCACAGAGG TAACAAC                                27

(2) INFORMATION FOR SEQ ID NO:4:

(i) SEQUENCE CHARACTERISTICS:
      (A) LENGTH: 27 base pairs
      (B) TYPE: nucleic acid
      (C) STRANDEDNESS: single
      (D) TOPOLOGY: linear    (xi) SEQUENCE DESCRIPTION: SEQ ID NO:4:

GAAGATCTTC GGCGGTGGAG CGAGTGC                                27